United States Patent [19]

Bergfeld et al.

[11] Patent Number: 4,831,171

[45] Date of Patent: May 16, 1989

[54] PROCESS FOR SYNTHESIZING AN AMMONIA COMPLEX OF ZINC BISDITHIOCARBAMATE

[75] Inventors: Manfred Bergfeld, Erlenbach-Mechenhard; Ludwig Eisenhuth, Obernburg, both of Fed. Rep. of Germany

[73] Assignee: Akzo N.V., Arnhem, Netherlands

[21] Appl. No.: 911,365

[22] Filed: Sep. 25, 1986

[30] Foreign Application Priority Data

Sep. 26, 1985 [DE] Fed. Rep. of Germany ....... 3534245

[51] Int. Cl.$^4$ .............................................. C07F 3/06
[52] U.S. Cl. .................................................. 556/134
[58] Field of Search ...................... 260/513.5; 556/134

[56] References Cited

U.S. PATENT DOCUMENTS 2,844,623 7/1958 Fike ..................................... 260/500
3,441,581 4/1969 Windel et al. .................... 260/429.9

FOREIGN PATENT DOCUMENTS 195440 2/1958 Austria .
1226361 4/1967 Fed. Rep. of Germany .
795142 5/1958 United Kingdom .

OTHER PUBLICATIONS

CIPAC Handbook, 1970, I, pp. 706–715.

*Primary Examiner*—Nicky Chan
*Attorney, Agent, or Firm*—Oliff & Berridge

[57] ABSTRACT

A process for synthesizing ammonia complexes of zinc bisdithiocarbamates, starting from carbon disulfide, ammonia, an alkylenediamine and zinc oxide, in which an aqueous mixture of alkylenediamine, carbon disulfide and ammonia in the molar ratio of 1:2:<2, i.e., not 1:2:2, as would be necessary for synthesis of the ammonium alkylene bisdithiocarbamate intermediate product, is reacted with zinc oxide.

4 Claims, 2 Drawing Sheets

PROCESS FOR SYNTHESIZING AN AMMONIA COMPLEX OF ZINC BISDITHIOCARBAMATE

BACKGROUND OF THE INVENTION

A. Field of the Invention

The invention relates to a process for synthesizing ammonia complexes of zinc alkylene bisdithiocarbamates starting from carbon disulfide, ammonia, an alkylenediamine and zinc oxide.

B. Description of the Prior Art

Such products are known as fungicides, especially zinc ethylene bisdithiocarbamate, also known as "Zineb". According to West German Pat. No. 1,226,361 ammonia complexes of zinc ethylene bisdithiocarbamate it can be synthesized in the following ways:

(a) from the Zineb.2NH$_3$ complex by acidification;

(b) from an aqueous Zineb suspension by prolonged stirring with an aqueous ammonia solution; and (c) from a water-soluble salt of ethylene bisdithiocarbamic acid by reaction with a water-soluble zinc salt in the presence of 1 mole of ammonia per mole of zinc salt.

In addition, Austrian Pat. No. 195,440 teaches the following methods of synthesis:

(d) reacting an aqueous solution of ammonium ethylene bisdithiocarbamate with zinc oxide; and (e) allowing zinc oxide to react with the necessary quantities of the starting materials needed for the formation of ammonium dithiocarbamate.

Austrian Pat. No. 195,440 discusses only zinc ethylene bisdithiocarbamate, but does not disclose the ammonia complexes thereof. From the examples, is it not obvious whether any, or which, ammonia complexes are formed. Accordingly, it is unclear what must be done to obtain selectively the ammonia complex with one NH$_3$ molecule per zinc atom.

SUMMARY OF THE INVENTION

The object of the invention is to develop a process for synthesizing ammonia complexes of zinc alkylene bisdithiocarbamates with approximately one NH$_3$ molecule per zinc dithiocarbamate molecule, wherein the product is to be synthesized so as to obtain the highest possible purity in a simple and cost-effective way.

The invention is essentially characterized by the fact that alkylenediamine, carbon disulfide and ammonia are mixed in a molar ratio of $\frac{1}{2}<2$ in water and zinc oxide is added to this solution. It is therefore not necessary that ammonia be used in the proportion of 2 moles of NH$_3$ per 2 moles of CS$_2$ and 1 mole of alkylenediamine which is necessary for the formation of ammonium alkylene bisdithiocarbamate, as taught by Austrian Pat. No. 195,440.

DETAILED DESCRIPTION OF THE INVENTION

Figure 1:
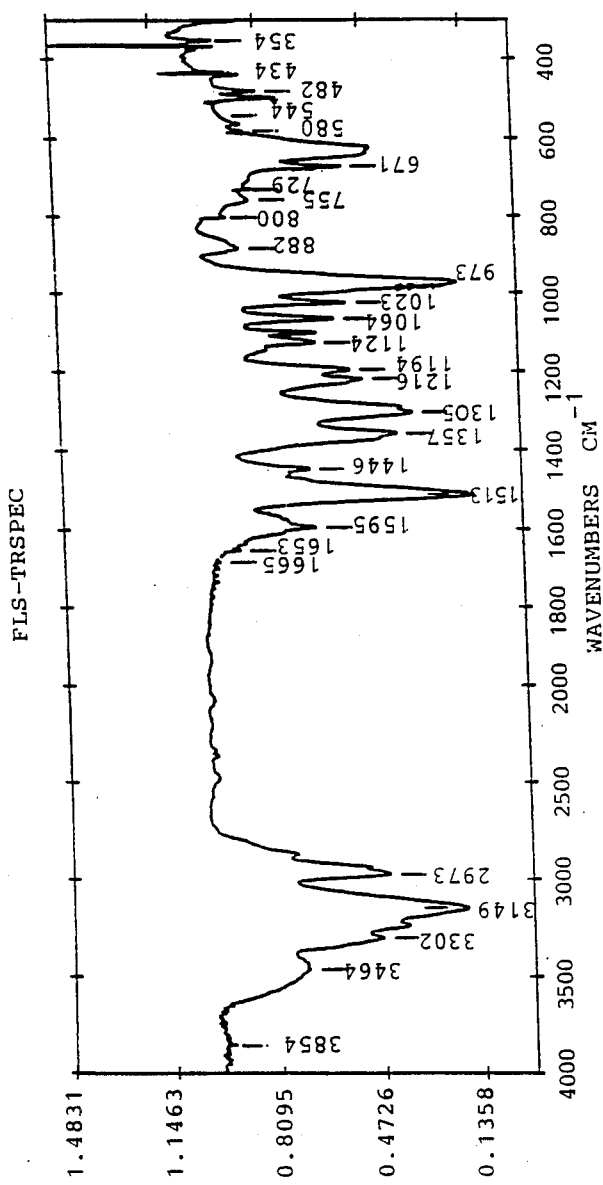
FIG. 1 shows the IR spectrum of the product from Example 1 (Zineb.NH$_3$).

The reaction can be summarized for example by the following equation:

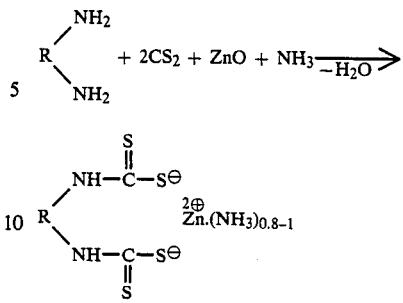

wherein R is C$_n$H$_{2n}$, and n is 2 to 6.

The general procedure is distinguished by its simplicity and is described as follows:

The carbon disulfide is added with vigorous stirring to an aqueous solution of alkylenediamine and ammonia in a reaction vessel, while the temperature is maintained below 30° C. The zinc oxide is then added and stirring is continued, during which the reaction temperature may range from 30° to 60° C. Depending on reaction temperature and stirring intensity, the reaction time is 1 to 6 hours. The reaction product is filtered off, washed with water if necessary, and dried.

Preferably, 2 moles of carbon disulfide as well as 0.6 to 1.5 moles of ammonia per mole of alkylenediamine are used. The zinc oxide is preferably used in stoichiometric quantities, but it can also be used in smaller quantities. On the other hand, zinc oxide used in excess will appear (as an impurity) in the product. The ammonia content of the zinc dithiocarbamate products depends on the quantity of ammonia used; in general, the ammonia content is approximately 0.8 to 1 mole per mole of zinc dithiocarbamate.

The products obtained are characterized by IR measurement, elemental analysis, CS$_2$ determination by the method of CIPAC Handbook, 1970, 1, p. 706 and NH$_3$ determination (titrimetric determination of the ammonia liberated with sodium hydroxide). Yields of up to 97% as well as product purities of up to 97% were achieved through this process.

The following embodiments are preferred: Aliphatic diamines with 2 to 6 C atoms can be used. Preferably, an aliphatic 1,2-diamine, especially ethylenediamine or propylenediamine, is used.

Advantageously, the reaction is performed with vigorous stirring in an aqueous medium. The presence of surfactants is also beneficial.

Commercial zinc oxide without any pretreatment was used for the process. As expected, it is advantageous to use zinc oxide having the smallest possible particle size (particles <0.1 mm).

Unexpectedly, according to the invention, it was possible to obtain the ammonia complex of zinc alkylene bisdithiocarbamate in a simple and economical way by using carbon disulfide and ammonia in a molar ratio of 2:<2. Therefore, the quantities of starting materials necessary for the formation of ammonium dithiocarbamate are not needed. Despite the lower concentration of ammonia, higher yields and better product qualities are obtained. Moreover, the preceding synthesis of the ammonium ethylene bisdithiocarbamate intermediate is no longer necessary.

Furthermore, the process of the invention has the advantage that the mother liquor can be recirculated, resulting in substantial savings of materials as well as a large reduction in the waste load.

The product obtained can be used directly as a fungicide. It is also possible to blend the products with other compounds, for example with manganese ethylene bisdithiocarbamate. The product obtained can also be cross-linked with formaldehyde.

The invention will be illustrated in greater detail by the following examples:

EXAMPLE 1

1 mole of carbon disulfide is added with vigorous stirring to a solution of 0.5 moles of ethylenediamine and 0.5 moles of ammonia in 200 g of water together with a few drops of Serdox NOP 9* in a glass reaction vessel, while the temperature is maintained below 30° C. After 15 minutes of further stirring, 0.5 moles of zinc oxide was added and stirring was continued for 2.5 hours at 40° C. The resulting white precipitate was filtered off, washed with water and dried at 50° C. In this way 135.4 g of a product is obtained which is identical in its infrared analysis (FIG. 1) with the ammonia complex of zinc ethylene bisdithiocarbamate ("Zineb"), which is described in West German Pat. No. 1,226,361. The yield of Zineb.NH$_3$ is 92.6% of theoretical, and the product purity is 96.1% (determined by CS$_2$ analysis).
*Nonylphenylpolyethylene glycol (Chemische Fabrik Servo b.v., Delden, The Netherlands).

| Analysis: | found (%) | calculated (%) |
|---|---|---|
| C | 16.6 | 16.4 |
| H | 3.1 | 3.1 |
| N | 14.0 | 14.4 |
| CS$_2$ | 50.0 | 52.0 |
| NH$_3$ | 5.0 | 5.8 |

The mother liquor still contains small quantities of unreacted carbon disulfide, ethylenediamine and ammonia starting materials, and therefore can be reused.

EXAMPLE 2 (COMPARISON EXAMPLE)

In this example the same procedure as in Austrian Pat. No. 195,440 is used.

40.7 g of ZnO (purity >99%) is introduced into a glass flask, and 250 ml of water containing 0.3 g of sodium ligninsulfonate is added. This slurry-formation process is performed for 15 minutes. Then, 82 g of carbon disulfide is introduced rapidly. Vigorous stirring is performed for a few minutes, whereupon a mixture consisting of 39 g of ethylenediamine and 68 g of aqueous ammonia (25 weight percent) is added dropwise with continuous vigorous stirring over a period of one hour. The temperature is maintained at 30° to 35° C. by a water bath. After the addition of both bases has been completed, the reaction is allowed to proceed three more hours. The product is filtered, washed with water and dried at 50° C.

Figure 2:
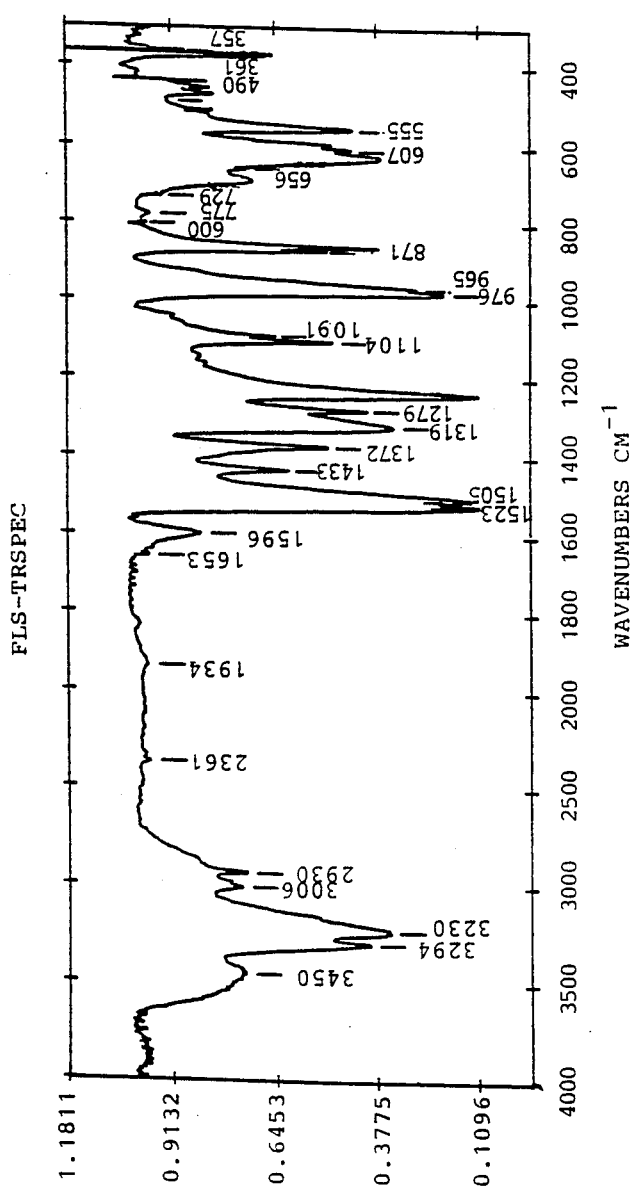
FIG. 2 shows the product from the Comparison Example 2 (Austrian Pat. No. 195,440).

Yield: 144.6 g. According to the IR spectrum (FIG. 2), neither Zineb nor Zineb.NH$_3$ is present. Moreover, the analysis data differ greatly from the values calculated for Zineb.NH$_3$. The structure of the substance was not elucidated.

| Analysis: | found (%) |
|---|---|
| C | 18.0 |
| H | 3.8 |
| N | 15.5 |

| Analysis: | found (%) |
|---|---|
| CS$_2$ | 43.2 |
| NH$_3$ | 5.1 |

Thus, this process does not lead to the desired Zineb.NH$_3$ product.

EXAMPLE 3

As described in Example 1, 2 moles of ethylenediamine, 4 moles of carbon disulfide and 2 moles of ammonia in 680 g of water were caused to react with 2 moles of zinc oxide. After addition of the zinc oxide, stirring was continued for 1 hour at 30° C. and 1 hour at 40° C. The Zineb.NH$_3$ product is obtained in a yield of 554.7 g (corresponding to 94.8% of theoretical); the content of Zineb.NH$_3$ is around 93.4%.

EXAMPLE 4 (COMPARISON EXAMPLE)

In this example, ammonium ethylene bisdithiocarbamate is synthesized first and is then reacted with ZnO as in Austrian Pat. No. 195,440 (Example 1).

The ammonium ethylene bisdithiocarbamate was synthesized by the process described in U.S. Pat. No. 2,844,623. 4 moles of ammonia and 2 moles of ethylenediamine are placed beforehand in 410 g of water containing a few drops of Serdox NOP 9, and 4 moles of carbon disulfide are added dropwise with stirring over a period of 1 hour (temperature: 30° to 35° C.). Thereafter, stirring is continued for one more hour at 35° to 38° C.

As in Example 1 of Austrian Pat. No. 195,440, 2 moles of zinc oxide are slurried for 10 min. in 540 g of water in a second reaction vessel. The above-synthesized ammonium ethylene bisdithiocarbamate solution is added to this slurry at room temperature, and stirring is continued for 1 hour. The temperature is maintained at 28° to 30° C. In this way 479.5 g of a product is obtained, which corresponds in its IR analysis to the Zineb.NH$_3$ complex (yield: 80.1% of theoretical; content of Zineb.NH$_3$: 90.2%).

EXAMPLES 5 TO 7

The procedure of Example 1 is followed, but the quantity of ammonia used is varied. The quantities of ammonia as well as the results obtained are listed below.

| Example | NH$_3$ (moles) | Product (g) | Zineb/NH$_3$ (content %) | NH$_3$ (weight %) |
|---|---|---|---|---|
| 5 | 0.75 | 141 | 95.8 | 5.4 |
| 6 | 0.4 | 134 | 95.5 | 4.6 |
| 7 | 0.3 | 126 | 94.4 | 3.7 |

EXAMPLE 8

1 mole of propylenediamine and 1.5 moles of ammonia are placed beforehand in 250 g of water. To this is added 2 moles of carbon disulfide at 20° to 30° C. and, after 30 minutes of vigorous stirring, 1 mole of zinc oxide is added. Thereafter, stirring is continued for 3 hours at 35° C., and the pale yellowish precipitate is filtered with suction, washed and dried. In this way 288.3 g of a product is obtained, which corresponds in its analysis to the ammonia complex of zinc propylenediamine bisdithiocarbamate (content on the basis of CS$_2$ analysis: 93.1%).

| Analysis: | found (%) | calculated (%) |
| --- | --- | --- |
| C | 19.1 | 19.6 |
| H | 3.7 | 3.6 |
| N | 13.9 | 13.7 |
| CS$_2$ | 46.1 | 49.6 |
| NH$_3$ | 4.8 | 5.5 |

What is claimed is:

1. A process for synthesizing ammonia complexes of zinc bisdithiocarbamates, comprising reacting an aqueous mixture of alkylenediamine, carbon disulfide and ammonia in a molar ratio of approximately 1:2:0.6–1.5, respectively, with zinc oxide.

2. The process according to claim 1, wherein the alkylenediamine is an aliphatic 1,2-diamine with 2 to 6 carbon atoms and primary amino groups.

3. The process according to claim 1, wherein the alkylenediamine is ethylenediamine.

4. The process according to claim 1, wherein the alkylenediamine is propylenediamine.

* * * * *